US007052702B1

(12) United States Patent
Duggan et al.

(10) Patent No.: US 7,052,702 B1
(45) Date of Patent: May 30, 2006

(54) CONJUGATES OF GALACTOSE-BINDING LECTINS AND CLOSTRIDIAL NEUROTOXINS AS ANALGESICS

(75) Inventors: Michael John Duggan, London (GB); John Andrew Chaddock, Hampshire (GB)

(73) Assignees: Health Protection Agency, Wiltshire (GB); Ipsen Limited, Berkshire (GB)

( * ) Notice: Subject to any disclaimer, the term of this patent is extended or adjusted under 35 U.S.C. 154(b) by 0 days.

(21) Appl. No.: 09/529,130

(22) PCT Filed: Oct. 7, 1998

(86) PCT No.: PCT/GB98/03001

§ 371 (c)(1),
(2), (4) Date: Jun. 22, 2000

(87) PCT Pub. No.: WO99/17806

PCT Pub. Date: Apr. 15, 1999

(30) Foreign Application Priority Data

Oct. 8, 1997 (GB) .................................... 9721189

(51) Int. Cl.
*A61K 39/68* (2006.01)
*C07K 14/00* (2006.01)

(52) U.S. Cl. .............................. 424/239.1; 424/236.1; 424/183.1; 424/194.1; 424/94.67; 435/69.1; 435/320.1; 435/252.7; 530/350; 530/396; 514/2; 514/12

(58) Field of Classification Search ............. 424/184.1, 424/194.1, 239.1, 236.1, 94.67, 832, 183.1; 435/252.7, 252.3, 320.1, 220, 69.1; 530/396, 530/300, 350; 514/2, 12
See application file for complete search history.

(56) References Cited

U.S. PATENT DOCUMENTS

| | | | |
|---|---|---|---|
| 4,792,447 A | 12/1988 | Uhr et al. ................. 424/85.91 |
| 4,873,346 A | 10/1989 | Anderson .................... 548/157 |
| 5,433,946 A | 7/1995 | Allen, Jr. et al. |
| 5,668,255 A | 9/1997 | Murphy |
| 5,721,207 A * | 2/1998 | Nobel et al. .................... 514/9 |
| 5,989,545 A | 11/1999 | Foster et al. ............. 424/183.1 |
| 6,235,313 B1 | 5/2001 | Mathiowitz et al. |
| 6,395,513 B1 | 5/2002 | Foster et al. |
| 6,461,617 B1 | 10/2002 | Shone et al. |
| 6,632,440 B1 | 10/2003 | Quinn et al. |
| 2003/0049264 A1 | 3/2003 | Foster et al. |
| 2003/0147895 A1 | 8/2003 | Shone et al. |
| 2003/0166238 A1 | 9/2003 | Shone et al. |
| 2004/0071736 A1 | 4/2004 | Quinn et al. |

FOREIGN PATENT DOCUMENTS

| | | |
|---|---|---|
| DE | 197 35 105 A1 | 3/1999 |
| EP | 0 602 686 A2 | 6/1994 |
| EP | 0 673 938 A2 | 9/1995 |
| WO | WO 91/09871 | 7/1991 |
| WO | WO 92/15327 | 9/1992 |
| WO | WO 93/04191 | 3/1993 |
| WO | WO 93/15766 | 8/1993 |
| WO | WO 94/21300 | 9/1994 |
| WO | WO 94/28923 | 12/1994 |
| WO | WO 95/17904 | 7/1995 |
| WO | WO 95/28171 | 10/1995 |
| WO | WO 95/32738 | 12/1995 |
| WO | WO 95/33850 | 12/1995 |
| WO | WO 96/12802 | 5/1996 |
| WO | WO 96/33273 | 10/1996 |
| WO | WO 97/13410 | 4/1997 |
| WO | WO 97/18790 | 5/1997 |
| WO | WO 98/07684 | 2/1998 |
| WO | WO 98/07864 | 2/1998 |
| WO | WO 98/08540 | 3/1998 |
| WO | WO 99/58571 | 11/1999 |
| WO | WO 00/04926 | 2/2000 |
| WO | WO 00/10598 | 3/2000 |
| WO | WO 00/57897 | 10/2000 |

OTHER PUBLICATIONS

Welch et al., Sensitivity of Embryonic Rat Dorsal Root Ganglia Neurons to *Clostridium botulinum* Neurotoxins. Toxicon 38, 245-258 (2000).*
Besson. The Complexity of Physiopharmacological Aspects of Pain. Drugs 53 Suppl 2, 1-9 (1997).*
Streit, W.J., et al., "Histochemical Localization of Galactose-Containing Glycoconjugates in Sensory Neurons and Their Processes in the Central and Peripheral Nervous System of the Rat," *J Histochem Cytochem* 33: 1042-1052 (1985).
Adar, R. et al., "The amino acid sequence of *Erythrina corallodendron* lectin and its homology with other legume lectins," *FEBS Lett.* 257:81-85 (1989), abstract from PubMed, PMID: 2806566.
Arango, R. et al., "Cloning and sequence analysis of the *Erythrina corallodendron* lectin cDNA," *FEBS Lett.* 264:109-111 (1990), abstract from PubMed, PMID: 1692539.

(Continued)

Primary Examiner—Jon Weber
Assistant Examiner—Chih-Min Kam
(74) *Attorney, Agent, or Firm*—Sterne, Kessler, Goldstein & Fox P.L.L.C.

(57) ABSTRACT

A class of novel agents that are able to modify nociceptive afferent function is provided. The agents may inhibit the release of neurotransmitters from discrete populations of neurones and thereby reduce or preferably prevent the transmission of afferent pain signals from peripheral to central pain fibers. They comprise a galactose-binding lectin linked to a derivative of a clostridial neurotoxin. The derivative of the clostridial neurotoxin comprises the L-chain, or a fragment thereof, which includes the active proteolytic enzyme domain of the light (L) chain, linked to a molecule or domain with membrane translocating activity. The agents may be used in or as pharmaceuticals for the treatment of pain, particularly chronic pain.

4 Claims, 7 Drawing Sheets

OTHER PUBLICATIONS

Arango, R. et al., "Expression of *Erythrina corallodendron* lectin in *Escherichia coli*," *Eur. J. Biochem.* 205:575-581 (1992), abstract from PubMed, PMID: 1572358.

Arora, N. et al., "Cytotoxic effects of a chimeric protein consisting of tetanus toxin light chain and anthrax toxin lethal factor in non-neuronal cells," *J. Biol. Chem.* 269:26165-26171 (1994), abstract from PubMed, PMID: 7929330.

Brinkmann, U. et al., "A recombinant immunotoxin containing a disulfide-stabiliz Fv fragment," *Proc. Natl. Acad. Sci. USA* 90:7538-7542 (1993), abstract from PubMed, PMID: 8356052.

Kurazono, H. et al., "Minimal Essential Domains Specifying Toxicity of the Light Chains of Tetanus Toxin and Botulinum Neurotoxin Type A," *J. Biol. Chem.* 267:14721-14729, The American Society for Biochemistry and Molecular Biology, Inc. (1992).

Lamb, F.I. et al., "Nucleotide sequence of cloned cDNA coding for preproricin," *Eur. J. Biochem.* 148:265-270 (1985), abstract from PubMed, PMID: 3838723.

Law, I. J., "Cloning and expression of cDNA for galactose-binding lectin from peanut nodules," *Plant Science* 115:71-79, Elsevier Science Ireland Ltd. (1996).

Lorberboum-Galski, H. et al., "Cytotoxic activity of an interleukin 2-Pseudomonas exotoxi chimeric protein produced in *Escherichia coli*," *Proc. Natl. Acad. Sci. USA* 85:1922-1926 (1988), abstract from PubMed, PMID: 3126499.

Murphy, J.R., "Diphtheria-related peptide hormone gene fusions: a molecular genetic approach to chimeric toxin development," *Cancer Treat. Res.* 37:123-140 (1988), abstract from PubMed, PMID: 2908622.

Nathan, S. and Halina, L., "Legume lectins—a large family of homologous proteins," *The FASEB J.* 4:3198-3208, The Federation of American Societies for Experimental Biology (1990).

"NeuroBloc (Botulinum Toxin Type B) For Cervical Dystonia Launched in UK," *Doctor's Guide*, P/S/L Consulting Group Inc. (Mar. 2001), visited <Nov. 28, 2001> at <http://www.pslgroup.com/dg/1F4216.htm>.

O'Hare, M. et al., "Cytotoxicity of a recombinant ricin-A-chain fusion protein containing a proteolytically-cleavable spacer sequence," *FEBS Lett.* 273:200-204 (1990), abstract from PubMed, PMID: 2121540.

Plank, C. et al., "The influence of endosome-disruptive peptides on gene transfer using synthetic virus-like gene transfer systems," *J. Biol. Chem.* 269:12918-12924 (1994), abstract from PubMed, PMID: 8175709.

Van Damme, E.J.M. et al., "Molecular cloning of the bark and seed lectins from the Japanese pagoda tree (*Sophora japonica*)," *Plant Molec. Biol.* 33:523-536, Kluwer Academic Publishers (1997).

Williams, D.P. et al., "Diphtheria toxin receptor binding domain substitution with interleukin-2: genetic construction and properties of a diphtheria toxin-related interleukin-2 fusion protein," *Protein Eng.* 1:493-498 (1987), abstract from PubMed, PMID: 3334101.

Wood, K.A. et al., "Preproabrin: genomic cloning, characterisation and the expression of the A-chain in *Escherichia coli*," *Eur. J. Biochem.* 198:723-732 (1991), abstract from PubMed, PMID: 2050149.

Yamaguchi, O. et al., "Chemical structures of two subunits, A-subunit and B-subunit, of galactose-specific isolectins from *Erythrina variegata* seeds," *J. Biochem* (*Tokyo*) 114:560-566 (1993), abstract from PubMed, PMID: 8276768.

Black, J.D., and Dolly, J.O., "Interaction of $^{125}$Labeled Botulinum Neurotoxins with Nerve Terminals. I. Ultrastructural Autoradiographic Localization and Quantitation of Distinct Membrane Acceptors for Types A and B on Motor Nerves," *J. Cell Biol.* 103:521-534, The Rockefeller University Press (1986).

Blaustein, R.O., et al., "The N-terminal half of the heavy chain of botulinum type A neurotoxin forms channels in planar phospholipid bilayers," *FEBS Letts.* 226:115-120, Elsevier Science Publishers B.V. (1987).

Shone, C.C., et al., "Inactivation of *Clostridium botulinum* type A neurotoxin by trypsin and purification of two tryptic fragments. Proteolytic action near the COOH-terminus of the heavy subunit destroys toxin-binding activity," *Eur. J. Biochem.* 151:75-82, Springer International (1985).

Shone, C.C., et al., "A 50-kDa fragment from the $NH_2$-terminus of the heavy subunit of *Clostridium botulinum* type A neurotoxin forms channels in lipid vesicles," *Eur. J. Biochem.* 167:175-180, Springer International (1987).

Sutton, J.M., et al., "Tyrosine-1290 of tetanus neurotoxin plays a key role in its binding to gangliosides and functional binding to neurones," *FEBS Letts.* 493:45-49, Elsevier Science B.V. (Mar. 2001).

Yamazaki, N., et al., "Endogenous lectins as targets for drug delivery," *Advanced Drug Delivery Reviews* 43:225-244, Elsevier Science B.V. (Sep. 2000).

Dialog File 351, WPI Accession No. 1999-168079/199915, Derwent WPI English language abstract for DE 197 35 105 A1 (Document AM2).

Diaz, A. and Dickenson, A.H., "Blockade of spinal N- and P-type, but not L-type, calcium channels inhibits the excitability of rat dorsal horn neurones produced by subcutaneous formalin inflammation," *Pain* 69:93-100, Elsevier Science Ireland Ltd. (Jan. 1997).

Edmonds, B.T. and Koenig, E., "Transmembrane Cytoskeletal Modulation in Preterminal Growing Axons: I. Arrest of Bulk and Organelle Transport in Goldfish Retinal Ganglion Cell Axons Regenerating In Vitro by Lectins Binding to Sialoglycoconjugates," *Cell Motil. Cytoskeleton* 17:106-117, Wiley-Liss, Inc. (1990).

Edmonds, B.T. and Koenig, E., "Transmembrane cytoskeletal modulation in preterminal growing axons. II. *Limax flavus* agglutinin-induced receptor redistribution, capping and internalization in varicosities of growing axons," *J. Neurocytol.* 20:232-247, Chapman and Hall Ltd. (1991).

Garber, N., et al., "On the specificity of the D-galactose-binding lectin (PA-I) of *Pseudomonas aeruginosa* and its strong binding to hydrophobic derivatives of D-galactose and thiogalactose," *Biochim. Et Biophys. Acta* 1116:331-333, Elsevier Science Publishers B.V. (1992).

Garret, C., et al., "Pharmacological properties of a potent and selective nonpeptide substance P antagonist," *Proc. Natl. Acad. Sci. USA* 88:10208-10212, National Academy of Sciences (1991).

Gupta, D., et al., "Differences in the Cross-Linking Activities of Native and Recombinant *Erythrina corallodendron* Lectin with Asialofetuin. Evidence for Carbohydrate-Carbohydrate Interactions in Lectin-Glycoprotein Complexes," *Biochem.* 33:2503-2508, American Chemical Society (1994).

Heilman, R.D., et al., "An Evaluation of the Hot Plate Technique to Study Narcotic Antagonists," *Res. Commun.*

*Chem. Pathol. Pharmacol. 13*:635-647, PJD Publications Ltd. (1976).

Iglesias, J.L., et al., "Purification and Properties of a D-Galactose/N-Acetyl-D-galactosamine-Specific Lectin from *Erythrina cristagalli,*" *Eur. J. Biochem. 123*:247-252, Blackwell Science Ltd. (1982).

Lembeck, F. and Holzer, P., "Substance P as Neurogenic Mediator of Antidromic Vasodilation and Neurogenic Plasma Extravasation," *Naunyn-Schmied. Arch. Pharmacol. 310*:175-183, Springer-Verlag (1979).

Lis, H. and Sharon, N., "Lectins as Molecules and as Tools," *Ann. Rev. Biochem. 55*:35-67, Annual Reviews, Inc. (1986).

Pintér, E., et al., "Lack of evidence for tachykinin $NK_1$ receptor-mediated neutrophil accumulation in the rat cutaneous microvasculature by thermal injury," *Eur. J. Pharmacol. 369*:91-98, Elsevier Science B.V. (Mar. 1999).

Silverman, J.D. and Kruger, L., "Selective neuronal glycoconjugate expression in sensory and autonomic ganglia: relation of lectin reactivity to peptide and enzyme markers," *J. Neurocytol. 19*:789-801, Chapman and Hall Ltd. (1990).

Sharon, N. and Lis, H., "Legume lectins—a large family of homologous proteins," *FASEB J. 4*:3198-3208, The Federation of American Societies for Experimental Biology (1990).

Welch, M. and Foster, K., "Chapter 26. Cell Culture of Neurons of the Peripheral Nervous System of Birds and Mammals," in: *The Neuron in Tissue Culture*, Haynes, L.W., ed., John Wiley & Sons Ltd., New York, N.Y. pp. 389-393 (Dec. 1999).

Zambenedetti, P., et al., "Identification of lectin binding sites in the rat brain," *Glycoconj. J. 13*:341-346, Chapman & Hall (Jun. 1996).

Zhou, L., et al., "Expression and Purification of the Light Chain of Botulinum Neurotoxin A: A Single Mutation Abolishes Its Cleavage of SNAP-25 and Neurotoxicity after Reconstitution with the Heavy Chain," *Biochem. 34*:15175-15181, American Chemical Society (1995).

Esp@cenet Database 12, English language abstract of European Patent No. 0 602 686 A2 (Document AO3).

Audet, M.A., Office Communication for U.S. Appl. No. 09/937,484, 12 pages, United States Patent and Trademark Office (mailed Jan. 29, 2004).

Schwartz, A.L., filing for U.S. Appl. No. 09/937,484, 4 pages; "Reply to Restriction Requirement" (filed Feb. 27, 2004).

Audet, M.A., Office Communication for U.S. Appl. No. 09/937,484, 16 pages, United States Patent and Trademark Office (mailed Jun. 21, 2004).

Schwartz, A.L., filing for U.S. Appl. No. 09/937,484, 14 pages, "Petition to the Director Under 37 C.F.R. §§ 1.144 and 1.181 to Withdraw Final Restriction Requirement" (filed Aug. 17, 2004).

Schwartz, A.L., filing for U.S. Appl. No. 09/937,484, 25 pages with Exhibits A-D, "Amendment and Reply Under 37 C.F.R. § 1.111" (filed Sep. 21, 2004).

Application and Prosecution History for "Recombinant Toxin Fragments," Shone et al., U.S. Appl. No. 09/255,829, filed Feb. 23, 1999.

Application and Prosecution History for "Methods and Compounds for the Treatment of Mucus Hypersecretion," Quinn et al., U.S. Appl. No. 09/763,669, with a §371 date May 29, 2001.

Application and Prosecution History for "Delivery of Superoxide Dismutase to Neuronal Cells," Shone et al., U.S. Appl. No. 09/831,050, with a §371 date of Aug. 20, 2001.

Application and Prosecution History for "Constructs for Delivery of Therapeutics Agents to Neuronal Cells," Shone et al., U.S. Appl. No. 10/130,973, with a §371 date of Jun. 25, 2002.

Application and Prosecution History for "Recombinant Toxin Fragments," Shone et al., U.S. Appl. No. 10/241,596, filed Sep. 12, 2002.

Application and Prosecution History for "Methods and Compounds for the Treatment of Mucus Hypersecretion," Quinn et al., U.S. Appl. No. 10/633,698, filed Aug, 5, 2003.

Shone et al., "Delivery of Superoxide Dismutase to Neuronal Cells," U.S. Appl. No. 11/062,471, filed Feb. 22, 2005.

Shone et al., "Recombinant Toxin Fragments," U.S. Appl. No. 11/077,550, filed Mar. 11, 2005.

Fisher, C.E., et al., "Genetic construction and properties of a diptheria toxin-related substance P fusion protein: *In vitro* destruction of cells bearing substance P receptors," *Proc. Natl. Acad. Sci. USA 93*:7341-7345, National Academy of Sciences USA (1996).

Hambleton, P., "*Clostridium botulinum* toxins: a general review of involvement in disease, structure, mode of action and preparation for clinical use," *J. Neurol. 239*:16-20, Springer-Verlag (1992).

Kurazono, H., et al., "Minimal Essential Domains Specifying Toxicity of the Light Chains of Tetanus Toxin and Botulinum Neurotoxin Type A," *J. Biol. Chem. 267*:14721-14729, American Society for Biochemistry and Molecular Biology, Inc. (1992).

Nishiki, T., et al., "Identification of Protein Receptor for *Clostridium botulinum* Type B Neurotoxin in Rat Brain Synaptosomes," *J. Biol. Chem. 269*:10498-10503, American Society for Biochemistry and Molecular Biology, Inc. (1994).

Nishiki, T., et al., "The high-affinity binding of *Clostridium botulinum* type B neurotoxin to synaptotagmin II associated with gangliosides $G_{T1b}/G_{D1a}$," *FEBS Lett. 378*:253-257, Federation of European Biochemical Societies (1996).

Poulain, B., et al., "Inhibition of transmitter release by botulinum neurotoxin A. Contributions of various fragments to the intoxication process," *Eur. J. Biochem. 185*:197-203, Federation of European Biochemical Societies (1989).

Zhou, L., et al., "Expression and purification of the Light Chain of Botulinum Neurotoxin A: A Single Mutation Abolishes Its Cleavage of SNAP-25 and Neurotoxicity after Reconstitution with the Heavy Chain," *Biochemistry 34*:15175-15181, American Chemical Society (1995).

International Search Report for PCT/GB99/02806, mailed Mar. 16, 2000.

Bizzini, B., "Investigation of the Mode of Action of Tetanus Toxin with the Aid of Hybrid Molecules Consisting in Part of Tetanus Toxin-Derived Fragments," *Bacterial Protein Toxins*, pp. 427-434, Academic Press London (1984).

Blaustein, R.O. et al., "The N-terminal half of the heavy chan of botulinum type A neurotoxin forms channels in planar phospholipid bilayers," *FEBS Letters 226*:115-120, Elsevier Science Publishers B.V. (Biomedical Division) (Dec. 1987).

Hay, D.W.P., "Chronic obstructive pulmonary disease:emerging therapies," *Current Opinion in Chemical Biology 4*:412-419, Elsevier Science Ltd. (Aug. 2000).

Madison, J.M., and Irwin, R.S., "Chronic obstructive pulmonary disease," *The Lancet 352*:467-473, The Lancet Publishing Group (Aug. 8, 1998).

Rogers, D.F., "Motor control of airway goblet cells and glands," *Respiration Physiology* 125:129-144, Elsevier Science B.V. (Mar. 2001).

Rogers, D.F., "Pharmacological regulation of the neuronal control of airway mucus secretion," *Current Opinion in Pharmacology* 2:249-255, Elsevier Science Ltd. (Jun. 2002).

Shone, C.C. et al., "A 50-kDa fragment from the $NH_2$-terminus of the heavy subunit of *Clostridium botulinum* type A neurotoxin forms channels in lipid vesicles," *Eur. J. Biochem.* 167:175-180, Springer International (Aug. 17, 1987).

Database—12, English language abstract of DE 197 35 105 A1, at esp@cenet.

Dialog File 351, Accession No. 2000-072332, Derwent WPI English language abstract for WO 99/58571.

Kielian, M., et al., Mechanisms of Mutations Inhibiting Fusion and Infection by Semliki Forest Virus, *J. Cell Biol.* 134:863-872, The Rockefeller University Press (1996).

Kihara, A., and Pastan, I., "Analysis of Sequences Required for the Cytotoxic Action of a Chimeric Toxin Composed of *Pseudomonas* Exotoxin and Transforming Growth Factor α," *Bioconjug. Chem.* 5:532-538, American Chemical Society (1994).

London, E., "Diphtheria toxin: membrane interaction and membrane translocation," *Biochim. Biophys. Acta* 1113:25-51, Elsevier Science Publishers B.V. (1992).

Murata, M., et al., "pH-Dependent Membrane Fusion and Vesiculation of Phospholipid Large Unilamellar Vesicles Induced by Amphiphilic Anionic and Cationic Peptides," *Biochemistry* 31:1986-1992, American Chemical Society (1992).

Picard-Maureau, M., et al., "Foamy Virus Envelope Glycoprotein-Mediated Entry Involves a pH-Dependent Fusion Process," *J. Virol.* 77:4722-4730, American Society for Microbiology (Apr. 2003).

Plank, C., et al., "The Influence of Endosome-disruptive Peptides on Gene Transfer Using Synthetic Virus-like Gene Transfer Systems," *J. Biol. Chem.* 269:12918-12924, The American Society for Biochemistry and Molecular Biology, Inc. (1994).

Prior, T.I., et al., "Translocation Mediated by Domain II of *Pseudomonas* Exotoxin A: Transport of Barnase into the Cytosol," *Biochemistry* 31:3555-3559, American Chemical Society (1992).

Seth, S., et al., "Activation of Fusion by the SER Virus F Protein: a Low-pH-Dependent Paramyxovirus Entry Process," *J. Virol.* 77:6520-6527, American Society for Microbiology (Jun. 2003).

Silverman, J.A., et al., "Mutational Analysis of the Helical Hairpin Region of Diphtheria Toxin Transmembrane Domain," *J. Biol. Chem.* 269:22524-22532, The American Society for Biochemistry and Molecular Biology, Inc. (1994).

Wagner, E., et al., "Influenza virus hemagglutinin HA-2 N-terminal fusogenic peptides augment gene transfer by transferrin-polylysine-DNA complexes: Toward a synthetic virus-like gene-transfer vehicle," *Proc. Natl. Acad. Sci. USA* 89:7934-7938, National Academy Press (1992).

Yao, Y., et al., "Membrane fusion activity of vesicular stomatitis virus glycoprotein G is induced by low pH but not by heat or denaturant," *Virology* 310:319-332, Academic Press (Jun. 2003).

\* cited by examiner

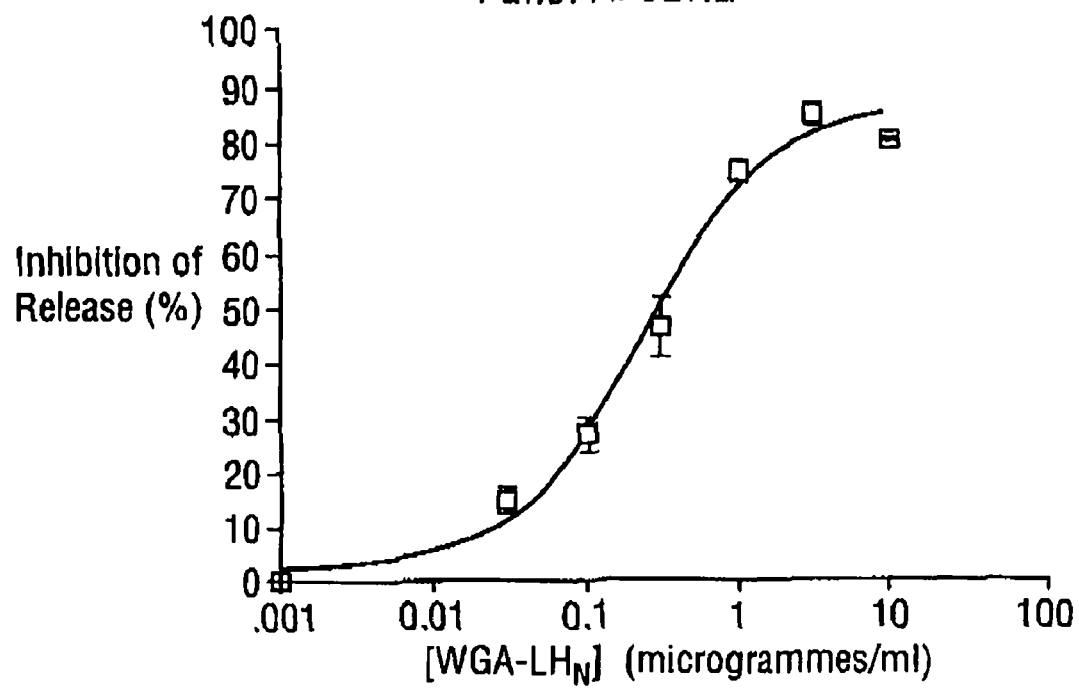
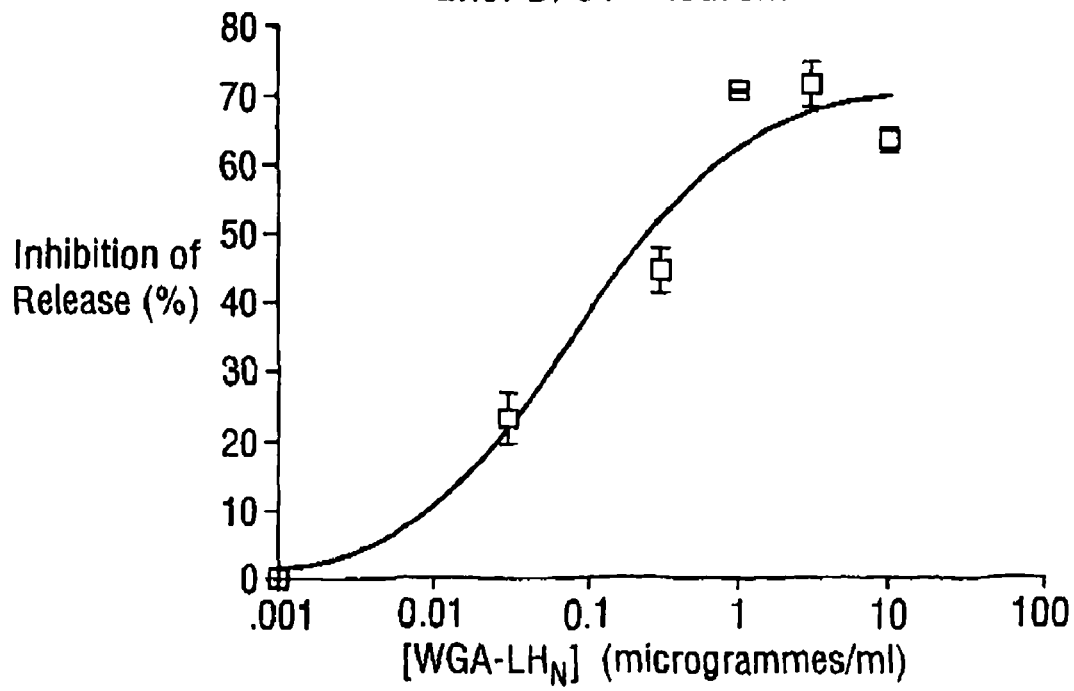

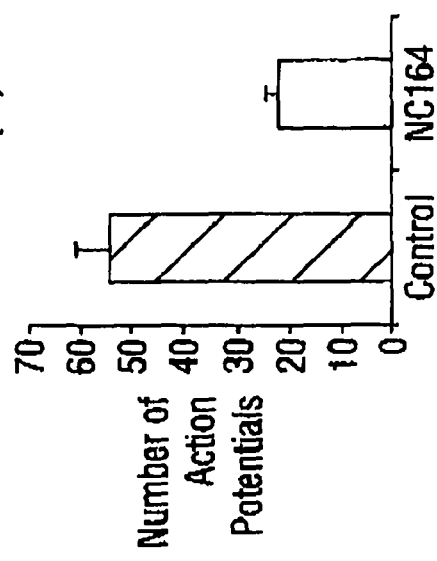
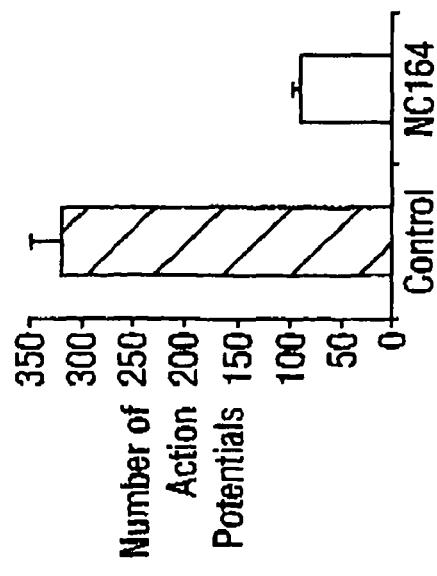
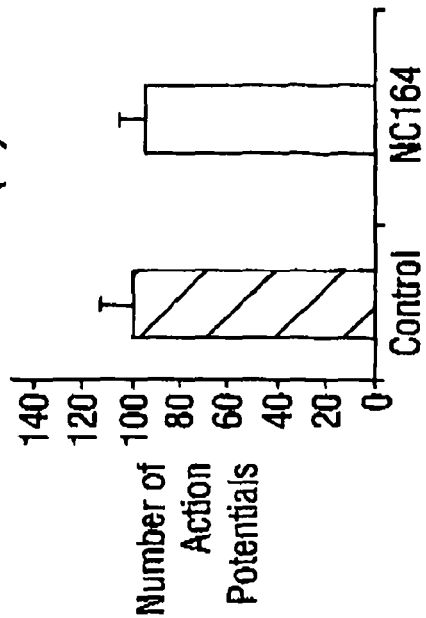
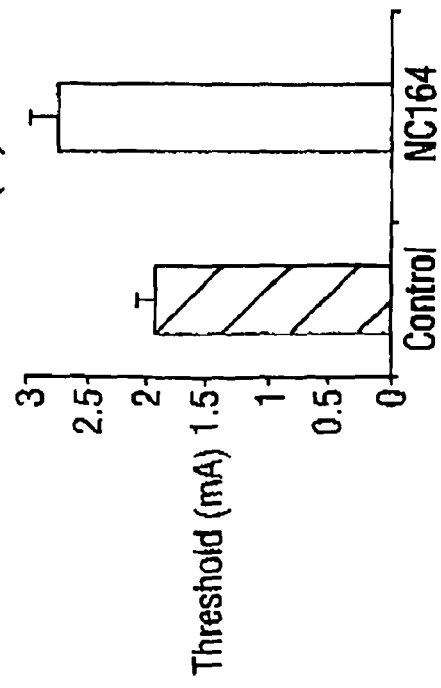

CONJUGATES OF GALACTOSE-BINDING LECTINS AND CLOSTRIDIAL NEUROTOXINS AS ANALGESICS

This application is a 371 of PCT/GB98/03001 filed Oct. 7, 1998, which claims the benefit of foreign priority under 35 U.S.C. §119(a)–119(d) to application United Kingdom 9721189.0 filed Oct. 8, 1997.

TECHNICAL FIELD

This invention relates to a class of novel agents that are able to modify nociceptive afferent function. The agents may inhibit the release of neurotransmitters from discrete populations of neurones and thereby reduce or preferably prevent the transmission of afferent pain signals from peripheral to central pain fibres. The agent may be used in or as a pharmaceutical for the treatment of pain, particularly chronic pain.

BACKGROUND

The sensation of pain due to injury or disease is carried from the periphery to the brain by a multi-neuronal pathway. The first part of this system comprises the primary nociceptive afferents that form synapses with secondary neurones in the dorsal horn of the spinal cord, or the nuclei of the cranial nerves. These synapses pass on the incoming information by the release of neurotransmitters and neuromodulators such as glutamate and substance P. These synapses are, therefore, possible sites for intervention to alleviate pain, indeed one of the modes of action of the opiate analgesics is to down-modulate neurotransmitter release at these synapses.

Unfortunately, the opiates have a number of limitations as drugs. Firstly, there are a number of chronic pain conditions for which the opiates are not effective. Secondly, the opiates have a number of side effects that are mediated both peripherally (constipation) and centrally (respiratory depression and euphoria) which present problems for long term use.

There is, therefore, a need for the development of new pharmaceuticals for the treatment of pain, particularly chronic pain.

One approach to this problem is the use of new agents containing fragments of clostridial neurotoxins (WO96/33273).

The clostridial neurotoxins are proteins with molecular masses of the order of 150 kDa. They are produced by various species of bacterium of the genus *Clostridium*, most importantly *C. tetani* and several strains of *C. botulinum*. There are at present eight different classes of the neurotoxins known: tetanus toxin, and botulinum neurotoxin in its serotypes A, B, $C_1$, D, E, F and G, and they all share similar structures and modes of action. The clostridial neurotoxins are synthesised by the host bacterium as single polypeptides that are modified post-translationally to form two polypeptide chains joined together by a disulphide bond. The two chains are termed the heavy chain (H), which has a molecular mass of approximately 100 kDa, and the light chain (L), which has a molecular mass of approximately 50 kDa. Two distinct functions can be identified within the H-chain; binding and translocation. The carboxy-terminal half ($H_C$) is involved in the high affinity, neurospecific binding of the toxin to cell surface acceptors, whilst the amino-terminal half ($H_N$) is central to the translocation of the toxin into the neuronal cell. For botulinum neurotoxin type A these-domains are considered to reside within amino acid residues 872–1296 for the $H_C$, amino acid residues 449–871 for the $H_N$ and residues 1–448 for the LC. The minimal domains necessary for the activity of the light chain of clostridial toxins are described in J. Biol. Chem. Vol.267, No.21, July 1992, pages 14721–14729. The eight distinct neurotoxin light chains (L) are highly specific zinc-dependent endopeptidases which each hydrolyse different but specific peptide bonds in one of three substrate proteins, synaptobrevin, syntaxin or SNAP-25. These substrates are important components of the neurosecretory machinery. The hydrolytic activity of the clostridial toxins results in a prolonged muscular paralysis. The functions of all three identified domains are necessary for the toxic activity of the clostridial endopeptidases.

Some of the clostridial endopeptidases, most notably botulinum neurotoxin type A, have been used as pharmaceutical agents for the treatment of a range of muscle dystonias. The flaccid paralysing action of the native botulinum toxins makes them appropriate for this use.

The use of fragments of clostridial neurotoxins for the desired purpose of analgesia is dependent on the invention of conjugates, or derivatives of these molecules, with a specific binding activity that will deliver the L-chain endopeptidase to the nociceptive afferent neurons in preference to other neurones in the relevant anatomical locus. Delivery of these conjugates includes binding to the cell surface, internalisation via an endosomal compartment and translocation of the clostridial endopeptidase activity into the cytosol.

Targeting of extracellular species to specific intracellular locations following endocytosis involves an appreciation of a number of possible targeting strategies. It is understood that early endosomes are part of the key sorting mechanisms of the cell, routing species to late endosome (and onto lysosomes for degradation), recycling to the cell surface or to the Trans-Golgi Network. Intracellular routing determinants have been suggested that determine the pathway and final destination of particular species (Mellman, 1996, Annu. Rev. Cell Biol., 12, 575–625).

Current data suggests that translocation of native clostridial neurotoxins occurs from an acidic intracellular compartment, though the exact location and nature of the compartment is unknown (Montecucco & Schiavo, 1994, Mol. Micro. 13, 1–8). In patent WO96/33273 it is proposed that for an agent to be effective, the agent must target to an appropriate compartment for translocation of the toxin. As an example of specific intracellular targeting, internalisation of the NGF-receptor is by specific endocytosis and retrograde routing (initiated by receptor-ligand complex), via acidic endosomes to the cell body, and an agent incorporating NGF is given in support of WO96/33273.

STATEMENT OF INVENTION

The present invention relates to an agent that can reduce and preferably prevent the transmission of pain signals from the periphery to the central nervous system, thereby alleviating the sensation of pain. Specifically, the invention can provide an agent that can reduce and preferably prevent the transmission of pain signals from nociceptive afferents to projection neurones. More specifically, the invention can provide an agent that can inhibit the exocytosis of at least one neurotransmitter or neuromodulator substance from at least one category of nociceptive afferents.

In one aspect of the invention, an agent is provided which can be administered to the spinal cord, and which can inhibit the release of at least one neurotransmitter or neuromodulator from the synaptic terminals of nociceptive afferents terminating in that region of the spinal cord.

In a second aspect of the invention, there is provided an agent which can specifically target defined populations of afferent neurones, so that the effect of the agent is limited to that cell type.

In a third aspect of the invention, there is provided a method of treatment of pain that comprises administering an effective dose of the agent according to the invention.

In a fourth aspect of the invention, the agent can be expressed recombinantly as a fusion protein that includes the required components of the agent.

Definitions

Without wishing to be limited by the definitions set down, it is intended in this description that the following terms have the following meanings:

Light chain means the smaller of the two polypeptide components of any of the clostridial neurotoxins. It is commonly referred to as the L-chain or simply L. An L-chain has a molecular mass of approximately 50 kDa, and it is a metalloprotease exhibiting high substrate specificity for vesicle and/or plasma membrane associated proteins involved in the exocytotic process.

Heavy chain means the larger of the two polypeptide components of any of the clostridial neurotoxins. It is commonly referred to as H-chain or simply H and has a molecular mass of approximately 100 kDa.

$H_C$ fragment means a peptide derived from the H-chain of a clostridial neurotoxin which is responsible for binding of the native holotoxin to cell surface acceptor(s) involved in the intoxicating action of clostridial toxin prior to internalisation of the toxin into the cell. It may be approximately equivalent to the carboxy-terminal half of the H-chain, or the domain corresponding to that fragment in the intact H-chain.

$H_N$ fragment means a fragment derived from the H-chain of a clostridial neurotoxin approximately equivalent to the amino-terminal half of the H-chain, or the domain corresponding to that fragment in the intact H-chain. It is characterised as:

A portion of the H-chain which enables translocation of that portion of the neurotoxin molecule such that a functional expression of light chain activity occurs within a target cell.

The domain responsible for translocation of the endopeptidase activity, following binding of neurotoxin to its specific cell surface receptor via the binding domain, into the target cell.

The domain responsible for formation of ion-permeable pores in lipid membranes under conditions of low pH.

The domain responsible for increasing the solubility of the entire polypeptide compared to the solubility of light chain alone.

$LH_N$ means a fragment derived from a clostridial neurotoxin that contains the L-chain, or a functional fragment thereof, coupled to a $H_N$ fragment.

BoNT/A means botulinum neurotoxin serotype A, and is a neurotoxin produced by *Clostridium botulinum*; it has a molecular mass of approximately 150 kDa.

$LH_N$/A is $LH_N$ that is derived from *Clostridium botulinum* neurotoxin type A.

Targeting Moiety (TM) means any chemical structure of an agent which functionally interacts with a binding site causing a physical association between the agent and the surface of a primary sensory afferent.

Primary sensory afferent is a nerve cell that can carry sensory information from the periphery towards the central nervous system.

Primary nociceptive afferent is a nerve cell that can carry sensory information from the periphery towards the central nervous system, where that information can result in a sensation of pain.

Lectin is any protein that binds to oligosaccharide structures.

Galactose-binding lectin is a lectin that binds to oligosaccharide structures in which the terminal residue is derived from galactose or N-acetylgalactosamine.

DETAILED DESCRIPTION OF THE INVENTION

It can be seen from this disclosure that an agent for reducing or preventing the transmission of pain signals from peripheral, nociceptive afferent neurones to projection neurones has many potential applications in the reduction of the sensation of pain, particularly of severe chronic pain.

Lectins are a class of proteins, often glycoproteins, that bind to carbohydrate structures. Lectins are found across the whole range of life forms from viruses to mammals. The most commonly exploited sources are the abundant lectins found in the seeds of plants. Lectins have previously been labelled and used as cell surface markers.

According to the invention, there is provided an agent that can inhibit the release of at least one neurotransmitter or neuromodulator or both from the synaptic terminals of nociceptive afferents.

It is known that such an agent can be produced based on the use of fragments of clostridial neurotoxin conjugated to a targeting ligand (WO96/33273). Given the known complexity of intracellular transport and the constraints on construct requirements, it is surprising that conjugates between toxin fragments and a specific sub-class of lectins that bind only to galactosyl residues form agents to produce analgesics that are particularly potent and selective. Inventions incorporating such lectins are the subject of this disclosure and several examples are provided.

One example of a class of plant-derived, galactose-binding lectins are those that can be purified from the seeds of the genus *Erythrina*. These lectins have been characterised to exist predominantly as non-covalent dimeric proteins with total molecular weights of approximately 60 kDa. Lectins have been isolated from several *Erythrina* species including: *E. corallodendron* (Gilboa-Garber and Mizrahi, 1981, Can. J. Biochem. 59, 315–320), *E. cristagalli* (Iglesias et al., 1982, Eur. J. Biochem. 123, 247–252), *E. indica* (Horejsi et al., 1980, Biochim. Biophys. Acta 623, 439–448), *E. arborescens, E suberosa, E. lithosperma* (Bhattacharyya et al., 1981, Archiv. Biochem. Biophys. 211, 459–470) *E. caffra, E. flabelliformis, E. latissima, E. lysistemon, E. humeana, E. perrieri, E. stricta*, and *E. zeyheri* (Lis et al., 1985, Phytochem. 24, 2803–2809).

These lectins have been analysed for their selectivity for saccharide binding (see e.g. Kaladas et al., 1982, Archiv. Biochem. Biophys. 217, 624–637). They have been found to bind preferentially to oligosaccharides with a terminal β-D-galactosyl residue.

A second example of a plant-derived, galactose-binding lectin with the desired binding specificity can be obtained from *Glycine max* (soy) beans. This lectin (soya bean agglutinin, SBA) is a tetrameric protein with a total molecular weight of approximately 110 kDa. It binds to oligosaccharides containing galactose or N-acetylgalactosamine residues.

An example of a galactose-binding lectin from bacteria is PA-I, obtained from *Pseudomonas aeruginosa*. PA-I is a D-galactosephilic lectin with a molecular weight of about 13 kDa and it binds to galactose-containing oligosaccharides (Gilboa-Garber and Mizrahi, 1981, Can. J. Biochem. 59, 315–320).

These and other lectins of the sub-class of galactose-binding lectins can be used as targeting moieties (TM) for conjugates of the type described in WO96/33273. The requirements for TMs in these agents are that they show specificity for the primary sensory afferents over other spinal nerves and that they lead to the internalisation of the agents into an appropriate intracellular compartment. The lectins of this invention fulfil these criteria. Surprisingly, in comparison to other lectins of WO96/33273, they can fulfil these criteria more efficiently and can provide agents with enhanced selectivity for nociceptive afferent neurosecretion.

Thus, in one embodiment of the invention a galactose-binding lectin is conjugated, using linkages that may include one or more spacer regions, to a derivative of the clostridial neurotoxins.

In another embodiment of the invention the agent is expressed in a recombinant form as a fusion protein. The fusion protein may be derived from nucleic acid encoding an appropriate fragment of a galactose-binding lectin, in addition to any desired spacer domains, with nucleic acid encoding all or part of a polypeptide of one serotype of neurotoxin. Such a nucleic acid may be a chimera derived from the nucleic acid encoding polypeptides from more than one serotype.

In another embodiment of the invention the required $LH_N$, which may be a hybrid of an L and $H_N$ from different clostridial toxin serotypes, is expressed as a recombinant fusion protein with the galactose-binding lectin, and may also include one or more spacer regions.

In a further embodiment of the invention the required TM, L or $LH_N$ and translocation domain components may be separately expressed in a recombinant form and subsequently linked, covalently or non-covalently, to provide the desired agent.

In a further embodiment of the invention the required translocation domain may be of a non-clostridial origin, comprising instead a peptide or other entity capable of similar or enhanced function. Examples would include, but not be restricted to, the translocation domain of diphtheria toxin (O'Keefe et al., Proc. Natl. Acad. Sci. USA (1992) 89, 6202–6206; Silverman et al., J. Biol. Chem. (1993) 269, 22524–22532), the translocation domain of *Pseudomonas* exotoxin type A (Prior et al. Biochemistry (1992) 31, 3555–3559), the translocation domains of anthrax toxin (Blanke et al. Proc. Natl. Acad. Sci. USA (1996) 93, 8437–8442) and a variety of fusogenic or hydrophobic peptides of translocating function (Plank et al. J. Biol. Chem. (1994) 269, 12918–12924).

Exploitation in Industry

The agent described in this invention can be used in vivo, either directly or as a pharmaceutically acceptable salt, for treatment of pain.

For example, an agent according to the invention can be administered by spinal injection (epidural or intrathecal) at the level of the spinal segment involved in the innervation of an affected organ for the treatment of pain. This is, for example, applicable in the treatment of deep tissue pain, such as chronic malignant pain.

The present invention will now be described by reference to the following examples together with the Figures that show the following:

FIG. 8, Panel A and FIG. 8, Panel B, show the activity of WGA-$LH_N$/A on release of neurotransmitter from eDRG and eSC neurons.

FIGS. 9(A)–9(D) show the activity of ExL-$LH_N$/A in an in vivo electrophysiology model of analgesia.

Figure 10:
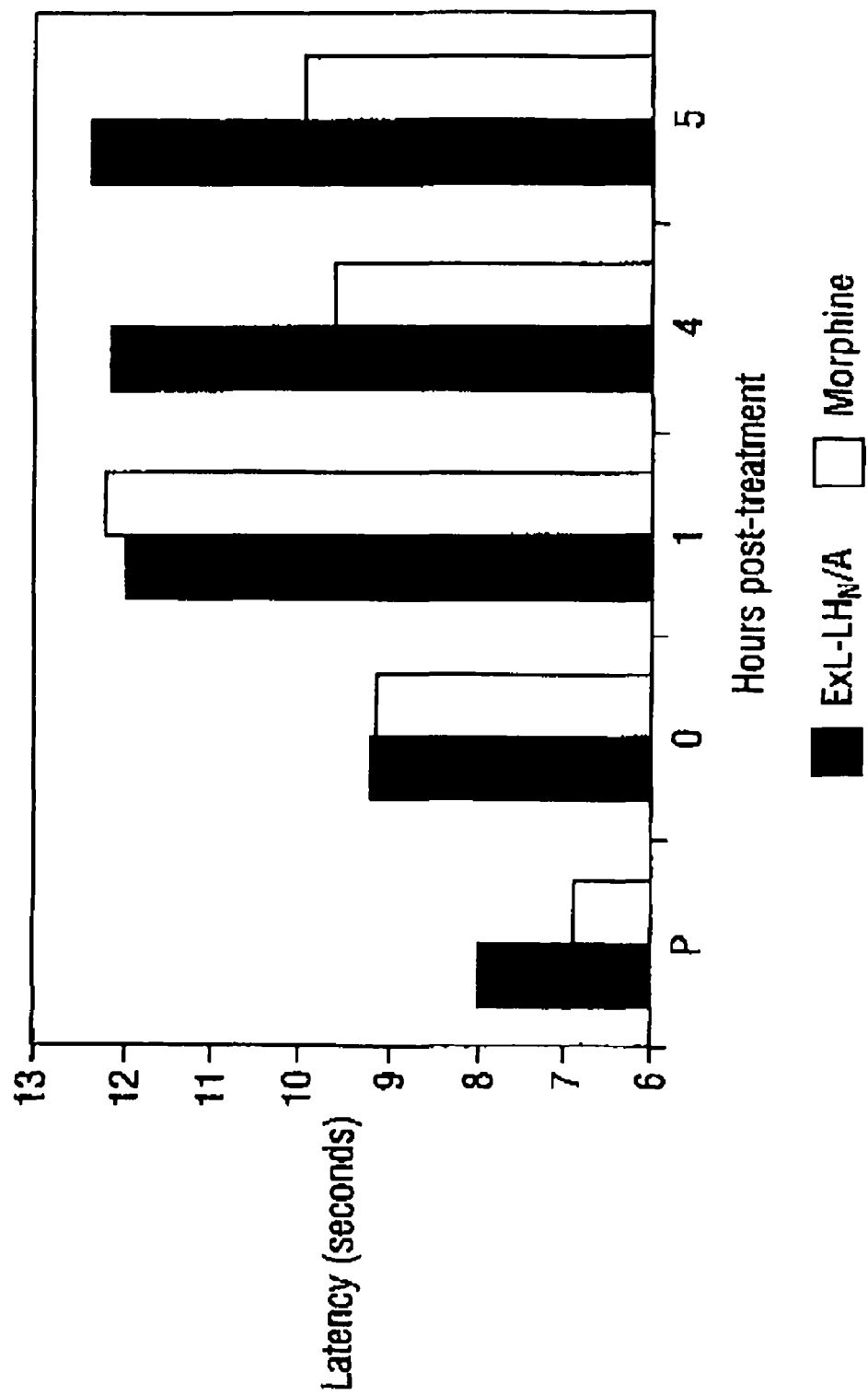

FIG. 10 shows the activity of ExL-$LH_N$/A in an in vivo behavioural model of analgesia.

EXAMPLE 1

The Production of a Conjugate Between a Lectin from *Erythrina cristagalli* and $LH_N$/A Materials Lectin from *E. cristagalli* (ExL) was obtained from Sigma Ltd.

$LH_N$/A was prepared essentially by the method of Shone C. C., Hambleton, P., and Melling, J. 1987, Eur. J. Biochem. 167, 175–180.

SPDP was from Pierce Chemical Co.

PD-10 desalting columns were from Pharmacia.

Dimethylsulphoxide (DMSO) was kept anhydrous by storage over a molecular sieve.

Denaturing sodium dodecylsulphate polyacrylamide gel electrophoresis (SDS-PAGE) was performed using gels and reagents from Novex Immobilised lactose-agarose was obtained from Sigma Ltd.

Additional reagents were obtained from Sigma Ltd.

Methods

The lyophilised lectin was rehydrated in phosphate buffered saline (PBS) to a final concentration of 10 mg/ml. Aliquots of this solution were stored at −20° C. until use.

The ExL was reacted with an equal concentration of SPDP by the addition of a 10 mM stock solution of SPDP in DMSO with mixing. After one hour at room temperature the reaction was terminated by desalting into PBS over a PD-10 column.

The thiopyridone leaving group was removed from the product by reduction with dithiothreitol (DTT, 5 mM, 30 min). The product of this reaction was analysed spectrophotometrically at 280 nm and 343 nm to determine the degree of derivatisation achieved. The degree of derivatisation achieved was 0.8±0.06 mol/mol. The thiopyridone and DTT were removed by once again desalting into PBS over a PD-10 column.

The $LH_N$/A was desalted into PBSE (PBS containing 1 mM EDTA). The resulting solution (0.5–1.0 mg/ml) was reacted with a four- or five-fold molar excess of SPDP by addition of a 10 mM stock solution of SPDP in DMSO. After 3 h at room temperature the reaction was terminated by desalting over a PD-10 column into PBS.

A portion of the derivatised $LH_N/A$ was removed from the solution and reduced with DTT (5 mM, 30 min). This sample was analysed spectrophotometrically at 280 mm and 343 nm to determine the degree of derivatisation. The degree of derivatisation achieved was 2.26±0.10 mol/mol. The bulk of the derivatised $LH_N/A$ and the derivatised ExL were mixed in proportions such that the ExL was in greater than three-fold molar excess. The conjugation reaction was allowed to proceed for >16 h at 4° C.

The product mixture was centrifuged to clear any precipitate that had developed. The supernatant was concentrated by centrifugation through concentrators (with 10000–50000 molecular weight exclusion limit) prior to a two step purification strategy. As the first step, the concentrated material was applied to a Superose 12 column on an FPLC chromatography system (Pharmacia). The column was eluted with PBS and the elution profile followed at 280 nm.

Fractions were analysed by SDS-PAGE on 4–20% polyacrylamide gradient gels, followed by staining with Coomassie Blue. The major band of conjugate has an apparent molecular mass of between 130–160 kDa; this is separated from the bulk of the remaining unconjugated $LH_N/A$ and more completely from the unconjugated ExL. Fractions containing conjugate were pooled prior to the second chromatography step; immobilised lactose-agarose. Selected post-Superose-12 fractions were applied to PBS-washed lactose-agarose and incubated for 2 hours at 4° C. to facilitate binding. Lectin-containing proteins (i.e. ExL-$LH_N/A$ conjugate) remained bound to the agarose during subsequent washing with PBS to remove contaminants (predominantly unconjugated $LH_N/A$). ExL-$LH_N/A$ conjugate was eluted from the column by the addition of 0.3 M lactose (in PBS) and the elution profile followed at 280 nm. The fractions containing conjugate were pooled, dialysed against PBS, and stored at 4° C. until use.

Figure 1:
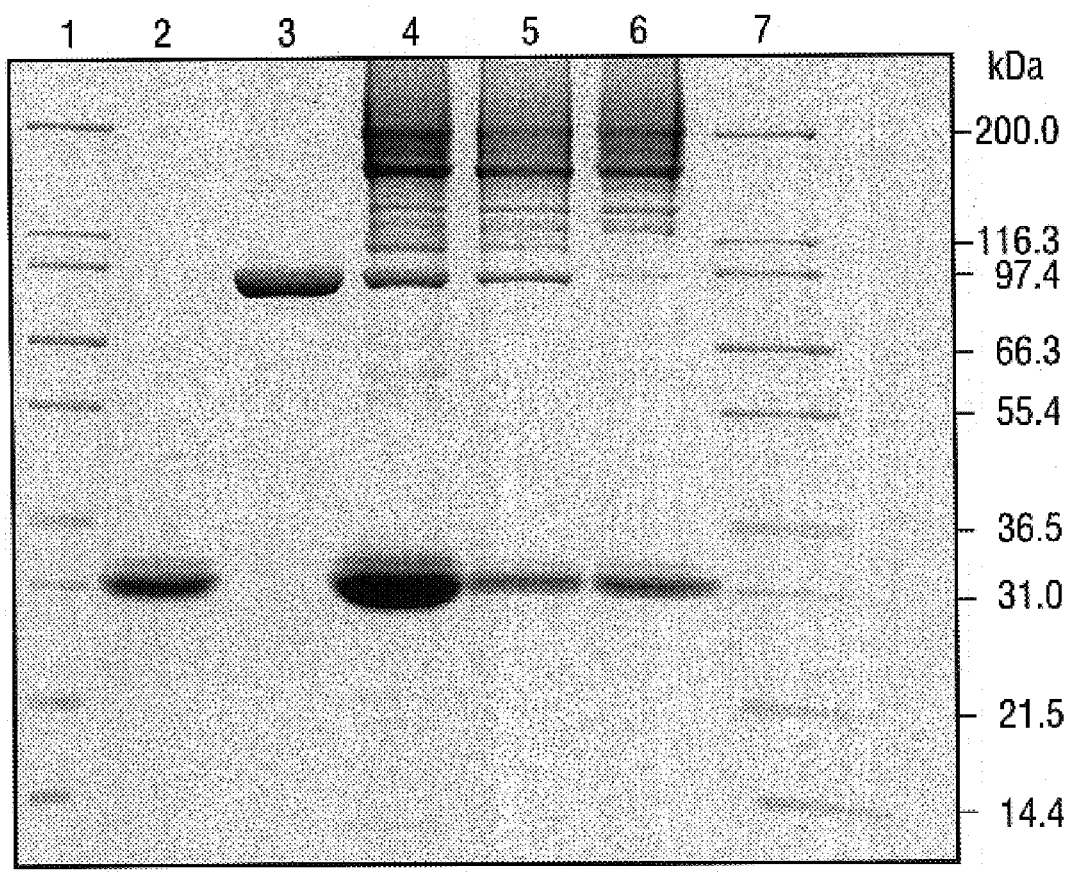
FIG. 1 shows an SDS-PAGE analysis of fractions from ExL-$LH_N$/A purification scheme.

In FIG. 1 is illustrated the SDS-PAGE profile during different stages in the conjugate purification scheme. Lanes 2 and 3 indicate ExL lectin and $LH_N/A$ respectively prior to conjugation. Lanes 4, 5 & 6 represent conjugation mixture, post-Superose-12 and post-lactose affinity chromatography samples respectively. Lane 6 is therefore indicative of the profile of the final conjugate material. Molecular weight markers are represented in lanes 1 & 7 with sizes indicated on the figure.

Figure 5:
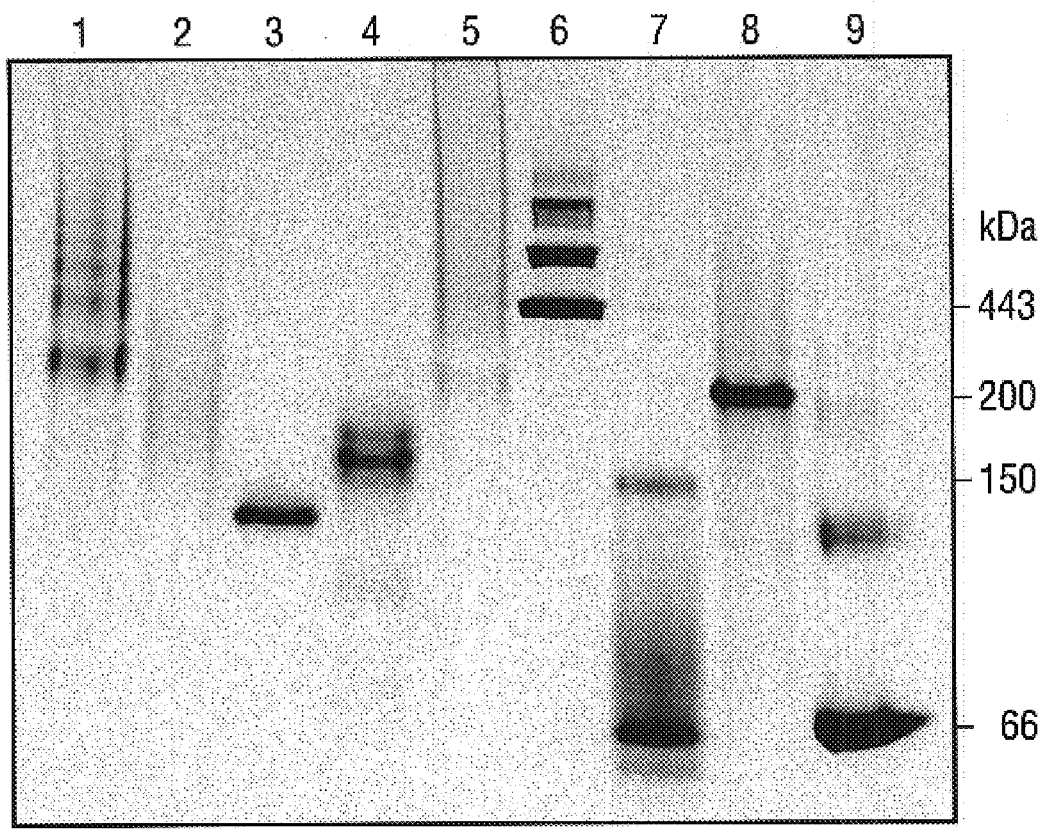
FIG. 5 shows native gel analysis of ExL- and SBA-$LH_N$/A.

On the SDS-PAGE gel there are bands due to lectin alone in fractions containing the conjugate, this material is probably due to the non-covalent homo-dimeric nature of the ExL; where only one monomer of ExL is covalently attached to the $LH_N/A$ the other is dissociated from the complex by the SDS in the electrophoretic procedure giving rise to these bands. The absence of free lectin monomers was confirmed by native PAGE analysis and is illustrated in FIG. 5. ExL-$LH_N/A$ (lane 5) was analysed by non-denaturing PAGE. Samples were separated using 4–20% polyacrylamide gel for 6.75 hours, 125V, 4° C. The electrophoresis profile was compared to those of $LH_N/A$ (lane 3) and ExL lectin only (lane 4). A range of marker proteins were analysed alongside; apoferritin (lane 6), β-amylase (lane 8), alcohol dehydrogenase (lane 7) and albumin (lane 9). Approximate molecular sizes are indicated.

EXAMPLE 2

The Production of a Conjugate Between a Lectin from *Erythrina corallodendron* and $LH_N/A$ The procedure for production of a conjugate between a lectin from *Erythrina corallodendron* and $LH_N/A$ is essentially as described in Example 1 but with the following differences:

Materials

Lectin from *E. corallodendron* (EcL) was obtained from Sigma Ltd.

Figure 3:
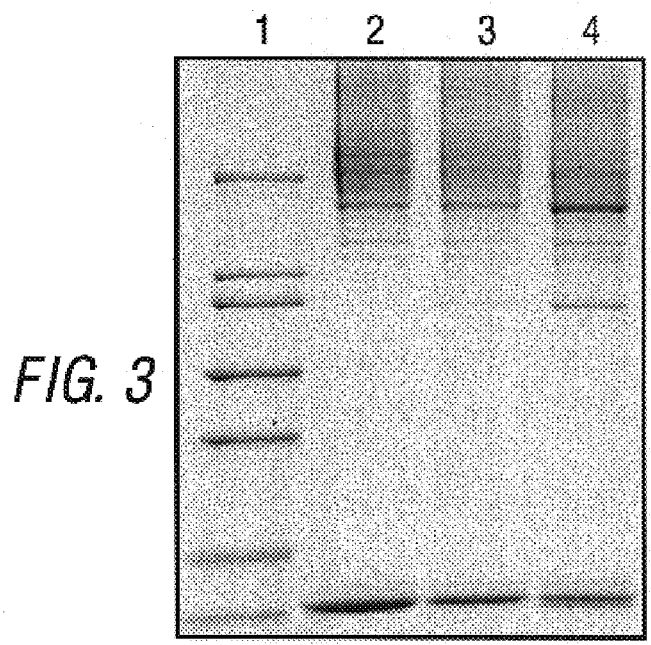
FIG. 3 shows an SDS-PAGE analysis of fractions from EcL-$LH_N$/A purification scheme.

FIG. 3 illustrates the purification scheme for the EcL-$LH_N/A$ conjugate. Samples were applied to 4–20% polyacrylamide gradient gels and subjected to electrophoresis prior to staining with Coomassie blue. Lane 1=molecular weight markers. Lane 2 represents the post-lactose affinity purified sample of EcL-$LH_N/A$. Lane 3 is a sample of pre-lactose affinity purified (size-exclusion chromatography only) EcL-$LH_N/A$. Lane 4 is a sample of pre-lactose affinity purified ExL-$LH_N/A$.

EXAMPLE 3

The Production of a Conjugate Between a Lectin from *Glycine max* and $LH_N/A$

The procedure for production of a conjugate between a lectin from *Glycine max* and $LH_N/A$ is essentially as described in Example 1 but with the following differences:

Materials

Lectin from *G. max* (SBA) was obtained from Sigma Ltd.

Method

Figure 4:
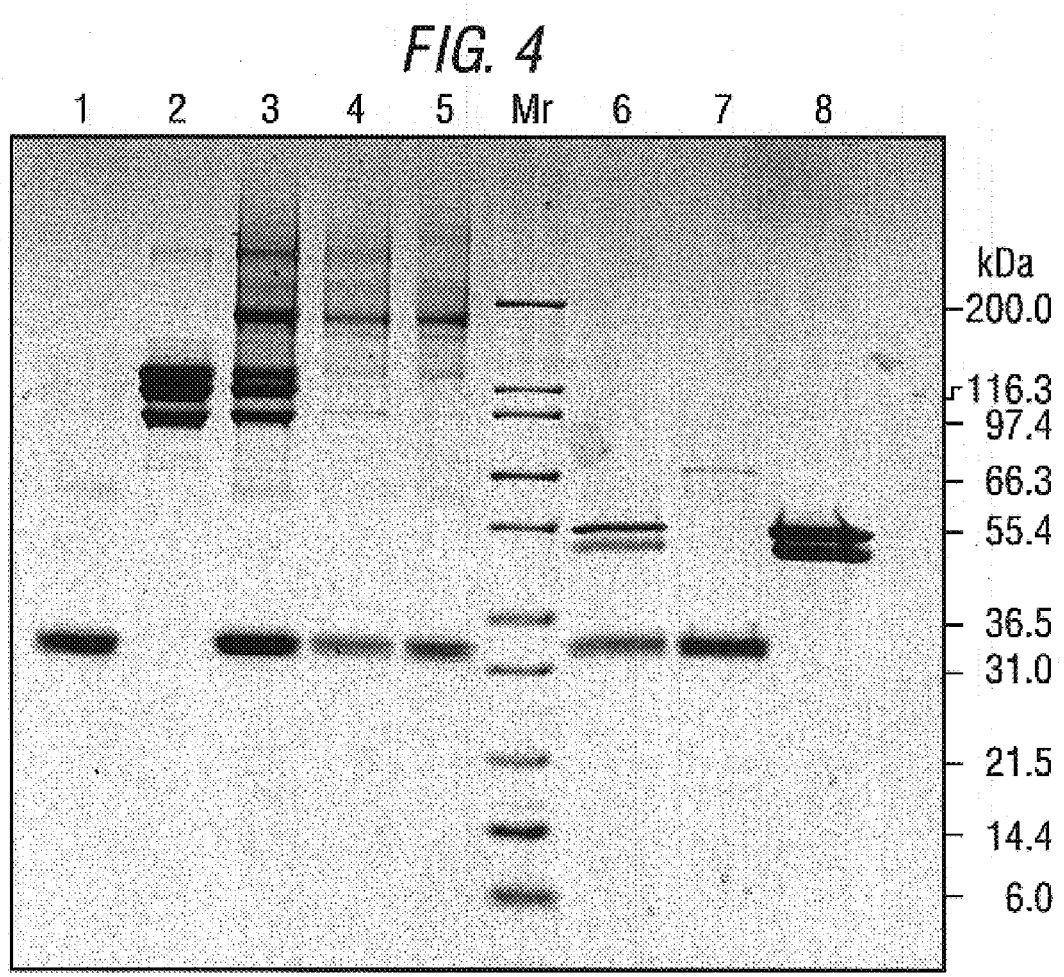
FIG. 4 shows an SDS-PAGE analysis of fractions from SBA-$LH_N$/A purification scheme.

For the affinity chromatography step an immobilised N-acetylgalactosamine (GalNAc) column was used and specific SBA-$LH_N/A$ was eluted by the addition of 0.3 M lactose. FIG. 4 illustrates SDS-PAGE profile changes during the purification scheme for SBA-$LH_N/A$. SBA-$LH_N/A$ was purified from crude conjugate mixture by Superose-12 size-exclusion chromatography and immobilised N-acetylgalactosamine affinity chromatography. Samples were subjected to SDS-PAGE on 4–20% polyacrylamide gels. Lanes 6–8 were run in the presence of 0.1 M DTT. Lanes 1 (&7) and 2 (&8) indicate SBA and SPDP-derivatised $LH_N/A$ respectively, prior to conjugation. Lanes 3, 4 & 5 (&6) represent conjugation mixture, post-Superose-12 and post-affinity chromatography samples respectively. Lane 5 is therefore indicative of the profile of the final conjugate material. Molecular weight markers are represented in lanes Mr with sizes indicated on the figure.

The absence of free lectin monomers was confirmed by native non-denaturing PAGE analysis as illustrated in FIG. 5. Samples were separated using 4–20% polyacrylamide gel for 6.75 hours, 125V, 4° C. The electrophoresis profile of SBA-$LH_N/A$ (lane 1) was compared to those of SBA lectin only (lane 2) and $LH_N/A$ (lane 3). A range of marker proteins were analysed alongside; apoferritin (lane 6), β-amylase (lane 8), alcohol dehydrogenase (lane 7) and albumin (lane 9). Approximate molecular sizes are indicated.

EXAMPLE 4

Activity of ExL-$LH_N/A$ in Primary Neuronal Cultures

The dorsal root ganglia contain the cell bodies of primary nociceptive afferent neurons. It is well established that in primary in vitro cultures of this tissue the neurons retain many of the characteristics of the nociceptive afferent. These characteristics include the ability to release neuropeptides such as substance P in response to chemical stimuli known to cause pain in vivo (e.g. capsaicin). Neurons anatomically adjacent to those of the DRG include those of the spinal cord. Cultures of SC neurons prepared from embryonic rats can be established in vitro and the release of neurotransmitter ($^3$H-glycine) under potassium stimulation can be assessed. As such, the eSC neurons represent a model cell for testing the selectivity of the agents described.

Figure 2:
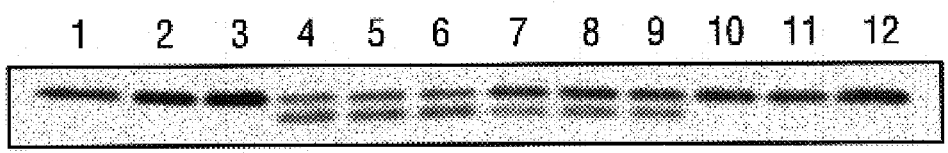
FIG. 2 shows cleavage of SNAP-25 by ExL-$LH_N$/A.
Figure 6:
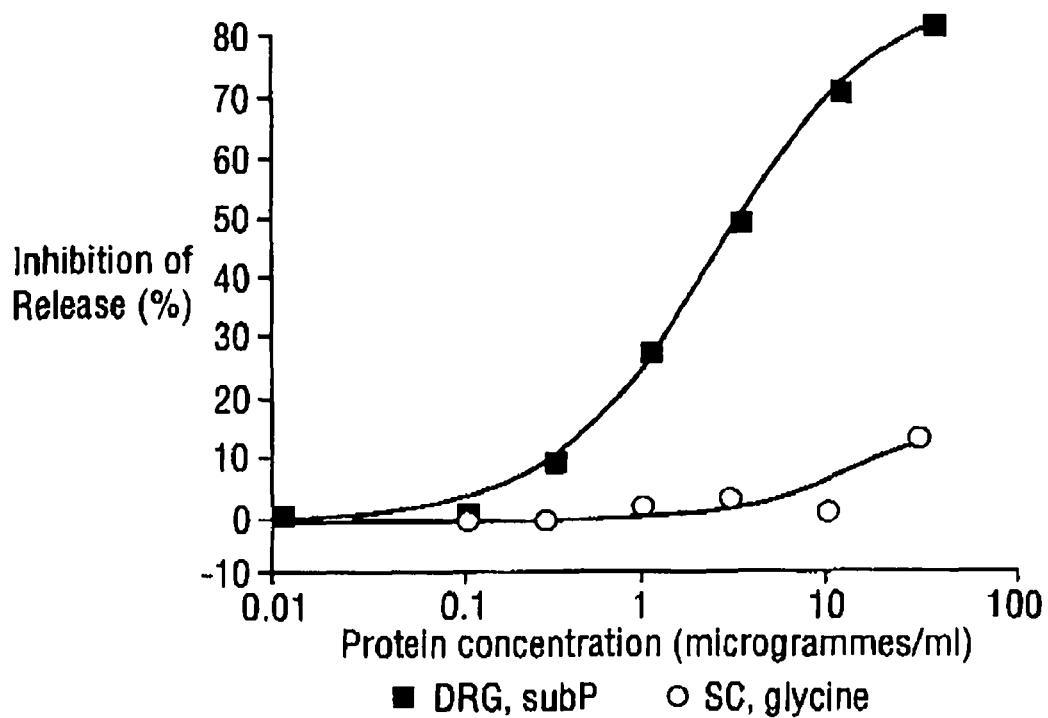
FIG. 6 shows the activity of ExL-$LH_N$/A on release of neurotransmitter from eDRG and eSC neurons.

The selectivity of the ExL-LH$_N$/A agent for eDRG over eSC neurons is clearly illustrated in FIG. 6. The dose curves document the effectiveness of ExL-LH$_N$/A in an in vitro cell culture model by comparing inhibition of neurotransmission in eDRG with eSC neurons.

Materials

Substance P enzyme linked immunosorbent assay kits were from Cayman Chemical Company.

Western blot reagents were obtained from Novex

Monoclonal antibody SMI-81 was from Sternberger Monoclonals Inc.

Methods

Primary cultures of dorsal root ganglion and embryonic spinal cord neurons were established following dissociation of the ganglia dissected from rat embryos (embryological age 12–15 days) For the preparation of eDRG neurons, the cells were plated into 12 well plates at an initial density of $3\times10^5$ cells/well in a medium containing NGF (100 ng/ml). After one day in culture, fresh medium containing cytosine arabinoside ($10\times10^{-6}$ M) was added to kill non-neuronal cells. After 2–4 days the cytosine arabinoside was removed. After several more days in culture the medium was replaced with fresh medium containing conjugate or $LH_N$.

For the preparation of eSC neurons, Cells were plated onto poly-D-lysine coated 12 well plates (Costar) at a density of $2\times10^6$ cells per well (1 ml/well). 'Plating' medium was MEM with Earles Salts (Sigma), containing 5% foetal bovine serum (FBS), 5% heat inactivated horse serum (HS), 0.6% dextrose, 1.5 g/l $NaHCO_3$ and 2 mM L-glutamine. Cultures are incubated at 37° C. with 10% $CO_2$. The medium was changed to 'feeding' medium (plating medium minus the FBS with N1 (Sigma) 1/50 supplement) after one day. When glial cells became almost confluent anti-mitotic agents (15 microgrammes/ml 5-fluoro-2'-deoxyuridine (FdU) and 35 microgrammes/ml uridine (U)) were added for a further 2–3 days. Cells were cultured for at least 3 weeks prior to use.

The cells were incubated with these agents for varying times and then tested for their ability to release the neurotransmitters glutamate and substance P (eDRG) or glycine (eSC). After the release assays were performed the cells were lysed and the hydrophobic proteins were extracted by phase partitioning with Triton-X-114 following the method outlined in Boyd, Duggan, Shone and Foster (J. Biol. Chem. 270, 18216–18218, 1995).

Substance P Release Assay

The release of endogenous substance P was effected by collecting cell supernatants after treating the cells for 5 min with either a physiological balanced salt solution or a balanced salt solution in which the potassium ion concentration had been raised to 100 mM with consequent reduction in the sodium ion concentration to maintain isotonicity. Total substance P was measured after extraction in 2 M acetic acid, 0.1% trifluoroacetic acid and subsequent dehydration. Substance P immunoreactivity was measured using an enzyme immunoassay kit (Cayman Chemical Company).

[$^3$H]Glutamate Release Assay

The release of glutamate was measured after loading the cells with [$^3$H]glutamine as a radiotracer. The [$^3$H]glutamine is converted to [$^3$H]glutamate in the cell, and it is this [$^3$H]glutamate that is taken up by synaptic vesicles and released upon depolarisation of the neuron. The cells are loaded with the [$^3$H]glutamine ($5\times10^{-6}$ Ci/ml in HEPES-buffered MEM) for 2 h, then washed twice with HEPES-buffered MEM and thrice with balanced salt solution (BSS). Basal release was assessed with a 3 min incubation with BSS. Stimulated release was determined by a 3 min incubation with BSS in which the potassium concentration had been elevated to 80–100 mM with a consequent reduction in the sodium concentration to maintain isotonicity. All manipulations were performed at 37° C. The cells were lysed by the addition of Triton-X-100 (0.1%, v/v). For the basal and stimulated release superfusates the glutamate was separated from the glutamine by ion-exchange chromatography over Dowex-1 resin. The relevant fractions were analysed for $^3$H content by liquid scintillation counting.

[$^3$H]Glycine Release Assay

The release of glycine was measured after loading the cells with [$^3$H]glycine as a radiotracer. The [$^3$H]glycine is taken up by synaptic vesicles and released upon depolarisation of the neuron. The cells are loaded with the [$^3$H] glycine ($2\times10^{-6}$ Ci/ml in HEPES-buffered MEM) for 2 h, then washed once with HEPES-buffered MEM and thrice with balanced salt solution (BSS). Basal release was assessed with a 5 min incubation with BSS. Stimulated release was determined by a 5 min incubation with BSS in which the potassium concentration had been elevated to 56 mM with a consequent reduction in the sodium concentration to maintain isotonicity. All manipulations were performed at 37° C. The cells were lysed by the addition of 2 M acetic acid, 0.1% trifluoroacetic acid. Fractions were analysed for their $^3$H content by liquid scintillation counting and inhibition of release determined.

FIG. 6 illustrates the activity of ExL-$LH_N$/A on release of neurotransmitter from eDRG and eSC neurons. Both eDRG and eSC cultures were exposed to a range of ExL-$LH_N$/A concentrations (1 ml volumes) for three days. The percentage inhibition of eDRG substance P (n) and eSC [$^3$H]-glycine (?) release is in comparison to untreated controls. The data shown is representative of =3 determinations. $IC_{50}$ for eDRG was determined to be 3.66±0.92 μg/ml. An inhibition of 50% was not obtained for eSC using the concentration range employed.

Western Blotting

ExL-$LH_N$/A was applied to eDRG for 16 hours. After the determination of neurotransmitter release the cells were lysed by the addition of 2 M acetic acid, 0.1% trifluoroacetic acid and subsequently dehydrated. To extract the membrane proteins from these mixtures Triton-X-114 (10%, v/v) was added and incubated at 4° C. for 60 min, the insoluble material was removed by centrifugation and the supernatants were then warmed to 37° C. for 30 min. The resulting two phases were separated by centrifugation and the upper phase discarded. The proteins in the lower phase were precipitated with chloroform/methanol for analysis by Western blotting.

The extracted protein samples were applied to 4–20% polyacrylamide gradient gels and subjected to electrophoresis prior to transfer to nitrocellulose. Proteolysis of SNAP-25, a crucial component of the neurosecretory process and the substrate for the zinc-dependent endopeptidase activity of BoNT/A, was then detected by probing with an antibody (SMI-81) that recognises both the intact and cleaved forms of SNAP-25 (FIG. 2). Proteins blotted onto nitrocellulose were probed with antibody SMI-81. Lanes 1–3, 4–6, 7–9 and 10–12 represent cells treated with medium, 40 microgrammes/ml ExL, 20 microgrammes/ml ExL and 40 microgrammes/ml $LH_N$/A respectively. Densitometric analysis of these data determined the % SNAP-25 cleavage to be 52.7% and 37.0% for 40 and 20 microgrammes/ml respectively.

EXAMPLE 5

Activity of SBA-$LH_N$/A in Primary Neuronal Cultures

Figure 7:
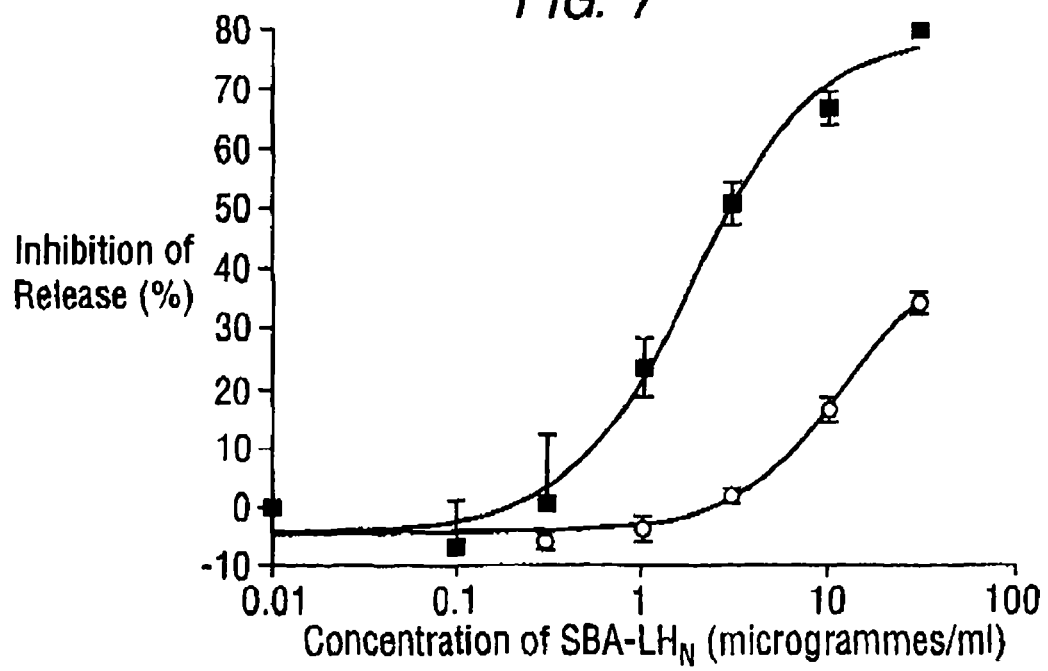
FIG. 7 shows the activity of SBA-$LH_N$/A on release of neurotransmitter from eDRG and eSC neurons.

Using methodology described in Example 4, the activity of SBA-$LH_N$/A in primary neuronal cultures was assessed. The selectivity of the SBA-$LH_N$/A conjugate for eDRG over eSC neurons is illustrated in FIG. 7. Both eDRG and eSC cultures were exposed to a range of SBA-$LH_N$/A concentrations (1 ml volumes) for three days. The percentage inhibition of eDRG substance P (n) and eSC [$^3$H]-glycine (O) release is in comparison to untreated controls. The data is the mean of three determinations ±SE. The curves shown are representative of two experiments. $IC_{50}$ values for eDRG neurons were determined to be 1.84 and 7.6 microgrammes/ml. It is observed that SBA-$LH_N$/A exhibits a clear selectivity of the inhibition of neurotransmitter release from eDRG relative to eSC neurons. These data therefore confirm observations described for ExL-$LH_N$/A above and highlight the properties of galactose-specific lectins.

EXAMPLE 6

Activity of WGA-$LH_N$/A in Primary Neuronal Cultures

Using methodology described in Example 4, the activity of WGA-$LH_N$/A in primary neuronal cultures was assessed. WGA represents an example of a non-galactosyl targeted lectin and therefore serves as an indicator of the properties of conjugate that do not recognise galactosyl moieties. The lack of selectivity of the WGA-$LH_N$/A conjugate for eDRG over eSC neurons is illustrated in FIG. 8, Panels A and B. eDRG and eSC neurons were exposed to a range of concentrations of WGA-$LH_N$/A for 3 days prior to assay of stimulated release of neurotransmitter (substance P and glycine respectively). Each conjugate concentration was assessed in triplicate and results are expressed as percentage inhibition compared to untreated controls. FIG. 8, Panels A and B, represent dose response curves from one experiment representative of ≧3 for eDRG and eSC neurons respectively. Each point shown is the mean of three determinations ±SE of the mean. $IC_{50}$ data for the effects of WGA-$LH_N$/A was calculated to be 0.34±0.06 microgrammes/ml (eDRG) and 0.06±0.09 microgrammes/ml (eSC), indicating the lack of C-fibre selectivity.

EXAMPLE 7

Activity of ExL-$LH_N$/A in an Electrophysiological Model of Pain

A dose of 45 microgrammes of ExL-$LH_N$/A in a 10 microlitres volume of vehicle was given by intrathecal injection to rats between lumbar sections L4–L5, 24 hours prior to electrophysiological analysis of neuronal activity. Animals were allowed to recover and movement was not restricted prior to sacrifice and analysis. The results from a group of 3 animals with 10 neurons recorded per animal, show that there was a 73% reduction in the C-fibre responses of the neurones (FIG. 9A) although the stimulus threshold is only slightly elevated (FIG. 9B). Inhibition of C-fibre responses would lead to a decrease in the transmission of pain signals and these data are indicative of the analgesic effect of conjugate ExL-$LH_N$/A. There was also a significant decrease in the $A_\delta$ response (FIG. 9C). These fibres are also implicated in the transmission of noxious stimuli and this result emphasises the analgesic effect of ExL-$LH_N$/A. $A_\beta$ neurons, a cell type that is not involved in transmission of noxious stimuli, were essentially unaltered in their responses to this stimulus (FIG. 9D). The lack of affect on the $A_\beta$-fibre neurons is indicative of the selectivity of ExL-$LH_N$/A for the neurons central to the transmission of pain signals.

EXAMPLE 8

Activity of ExL-$LH_N$/A in Behavioural Models of Pain

In an accepted in vivo model of pain, the mouse hotplate test, ExL-$LH_N$/A has been demonstrated to exhibit analgesic properties. FIG. 10 illustrates the data obtained for ExL-$LHd_N$/A where it is compared to a supramaximal dose of morphine. ExL-$LH_N$/A was applied intrathecally (30 microgrammes in a 5 microlitre vehicle volume) to each of a group of 10 mice and analgesic response in the hot plate test determined. Data is presented as hot plate latency (seconds) plotted against assay time (P=pre-treatment, 0–5=hours post application). Onset of ExL-$LH_N$/A action had apparently reached a plateau at 1 hour that remained constant for at least 5 hours. The level of analgesia is similar to a supramaximal dose (50 microgrammes, 20× mouse $EC_{50}$) of morphine in this test, but is of much longer duration. This level of morphine achieves a maximal effect at 1 hour and then returns to control levels over a period of 5 hours. These data represent a clear indication of the analgesic potential of agents such as ExL-$LH_N$/A.

Materials

Adult outbred mice (MF1) of either sex, weight range 20 to 30 g.

Methods

Test material is injected into the intrathecal space of anaesthetised mice using a 30 gauge disposable needle attached to a 50 microlitre Hamilton syringe. The site of injection was normally chosen to be between lumbar vertebrae 5 and 6. The needle is inserted into the tissue to one side of the vertebrae so that it slips into the groove between the spinous and transverse processes. The needle is then moved carefully forward to the intervertebral space. 5 microlitres of test material is then injected into the intrathecal space and the needle withdrawn. The skin incision is then closed with a single wound clip and the animal placed in a box to allow recovery.

The invention claimed is:

1. An agent for the treatment of pain, which comprises: a galactose-binding or an N-acetylgalactosamine-binding lectin; a light (L) chain or an L-chain fragment of a clostridial neurotoxin, which L-chain or L-chain fragment contains a proteolytically active enzyme domain of the L-chain; and the translocation domain of a clostridial neurotoxin H-chain; wherein the L-chain or L-chain fragment and the translocation domain of the clostridial neurotoxin H-chain are linked by disulfide bond to form $LH_N$, and wherein the $LH_N$ and the lectin are linked together by contacting the $LH_N$ and the lectin with one or more chemical coupling agents.

2. The agent according to claim 1, wherein the lectin is of bacterial origin.

3. The agent according to claim 2, wherein the lectin is obtained from *Pseudomonas aeruginosa*.

4. The agent according to claim 1, wherein the $LH_N$ and the lectin are linked by SPDP.

* * * * *